United States Patent
Watmough

(10) Patent No.: US 6,650,935 B1
(45) Date of Patent: Nov. 18, 2003

(54) ULTRASOUND DRIVEN DEVICES FOR ACCELERATED TRANSFER OF SUBSTANCES ACROSS POROUS BOUNDARIES

(76) Inventor: David J. Watmough, 16 Blackpark Terrace, Inverness (GB), IV3 SNE ( * ) Notice: Subject to any disclaimer, the term of this patent is extended or adjusted under 35 U.S.C. 154(b) by 0 days.

(21) Appl. No.: 09/806,900

(22) PCT Filed: Oct. 7, 1999

(86) PCT No.: PCT/GB99/03325

§ 371 (c)(1),
(2), (4) Date: Apr. 4, 2001

(87) PCT Pub. No.: WO00/21605

PCT Pub. Date: Apr. 20, 2000

(30) Foreign Application Priority Data

Oct. 9, 1998 (GB) .............................................. 9822150

(51) Int. Cl.[7] .................................................. A61N 1/30
(52) U.S. Cl. ......................................................... 604/20
(58) Field of Search ............................. 604/20, 22, 28, 604/500–501, 522, 19

(56) References Cited

U.S. PATENT DOCUMENTS

| | | | |
|---|---|---|---|
| 3,650,625 A | | 3/1972 | Hoyte, Jr. |
| 4,789,667 A | * | 12/1988 | Makino et al. .............. 514/161 |
| 5,267,985 A | | 12/1993 | Shimada et al. |
| 5,421,816 A | * | 6/1995 | Lipkovker .................... 604/20 |
| 5,438,954 A | * | 8/1995 | Phelps et al. ................ 119/6.8 |
| 5,658,247 A | * | 8/1997 | Henley ......................... 604/20 |
| 5,762,066 A | * | 6/1998 | Law et al. ............. 128/660.03 |
| 5,915,378 A | * | 6/1999 | Lloyd et al. ................ 128/200 |

FOREIGN PATENT DOCUMENTS

| | | |
|---|---|---|
| EP | 0495531 A1 | 7/1992 |
| WO | WO 94/08655 | 4/1994 |
| WO | WO 98/00194 | 1/1998 |
| WO | WO 98/17184 | 4/1998 |

* cited by examiner

*Primary Examiner*—Michael J. Hayes
*Assistant Examiner*—Ann Y Lam
(74) *Attorney, Agent, or Firm*—Carmody & Torrance LLP

(57) ABSTRACT

A method of phonophoretic transfer of an active agent into or across a porous surface, which method comprises contacting the active agent with the porous surface and applying thereto ultrasound at a frequency of between 20 kHz and 3 MHz; characterised in that the active agent is ideally cationic and is disposed in a low viscosity carrier and wherein the active agent is in direct contact with the porous surface. An apparatus for phonophoretic transfer of an active agent to or through a porous surface, said apparatus comprising an ultrasonic generator, a housing provided with an ultrasound transducer mounted in or on housing, and a treatment chamber disposed in or on said housing, said transducer being directed towards said treatment chamber, wherein the treatment chamber is provided with a liquid-tight membrane to retain the active agent against a porous surface located in the treatment chamber during sonication.

6 Claims, 8 Drawing Sheets

Figure 1:
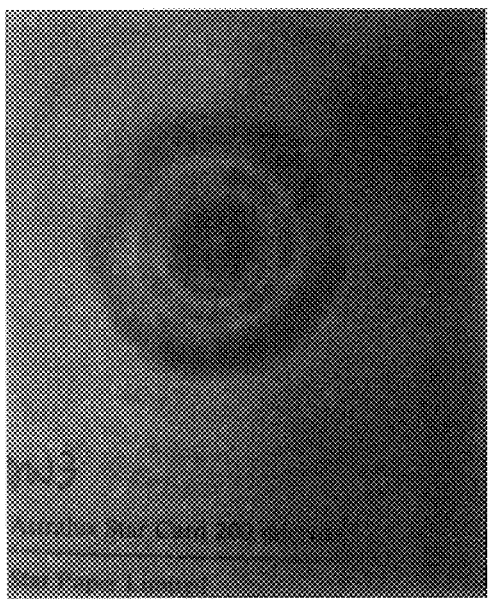

ULTRASOUND DRIVEN DEVICES FOR ACCELERATED TRANSFER OF SUBSTANCES ACROSS POROUS BOUNDARIES

The present invention relates to the delivery of active agents across or into a porous surface by ultrasound phonophoresis. Such a surface includes any interface which may be provided with microscopic channels or irregular spaces extending at least partially therethrough. Examples of present significance are human and animal skin, egg shells, certain vegetables, and printable cellulosic surfaces.

Ultrasound in the lower megahertz frequency range is used for diagnostic imaging, physiotherapy, hyperthermia and phonophoresis. Ultrasound-induced phonophoresis embraces, inter alia the transfer of biologically active agents (or chemical substances) at an enhanced rate through the skin or other porous surfaces. According to Williams, (Ultrasonics 1990, 28, 137–141) who tested three topical anaesthetic agents on the skin, phonophoresis did not occur if temperature effects were eliminated (i.e. he claims that enhanced diffusion rates were due simply to the temperature rise caused by sonication). Referring to some eighty previous reports, Williams et al in the same paper but at pages 132–136 state "a critical evaluation of the small number of observations on which these articles are based shows the inherent variability of the technique was so large that the observed distribution of results could simply have arisen by statistical chance". It can be concluded that as widely understood phonophoresis, if it occurs at all, is generated by moving an ultrasound activated transducer over the skin, and in contact with it, using a coupling gel or cream containing the material/drug that it is desired to deliver into the subdermal region. Clearly Williams raises strong doubts about the genuine nature of ultrasound-induced phonophoresis occuring under such circumstances. A recent patent [U.S. Pat. No. 5,421,816 Lipkovker] approaches the problem of transdermal drug delivery differently, but envisages a porous polymeric membrane enclosing the drug and the membrane is in contact with the skin. As we shall show in the following investigation efficient transfer using ultrasound preferably requires an aqueous solution of the drug which it is desired to deliver, to be in complete contact with the skin so that microbubbles generated by ultrasound can lodge on the skin close to hair follicles and sweat glands. The actions and properties of these acoustically induced bubbles are responsible for driving drugs at high transfer rates into porous surfaces.

Bearing in mind the desirability of being able to deliver certain biologically active agents such as drugs and anaesthetic preparations, in reasonable time scales, preferably in a period of a few seconds, without mechanically penetrating the skin or shell with a hypodermic needle, for example, plainly requires other mechanisms to achieve topical transfer.

Similarly there is commercial interest in the transfer into incubating chicken, duck and turkey eggs of various biologically active agents, for example Tylosin tartrate and Gentamycin, for control of Mycoplasma gallisepticum and Mycoplasma meleagridis respectively. Additionally there is an interest in transferring through intact egg shells antibacterial drugs of other types, live viral vaccines, hyperimmnune serum and nutrient supplements. Administration of an antibiotic to act against egg-transmitted infectious agents already has great value even though it currently requires puncturing the shell.

The treatment of incubating avian eggs by embryonal vaccination or the introduction of antibiotics by penetrative means has been described in U.S. Pat. Nos. 4,604,968, 4,458,630 and 4,681,063.

An instrument using penetration of the eggshell (Sharma et al., Disease control in Avian Species by Embryonal Vaccination U.S. Pat. No. 4,458,630) by mechanical means is marketed in the USA where the poultry industry has a turnover in excess of $20 billion. Mechanical penetration of the shell is undesirable as it may transfer infection between eggs and requires the needle to be repeatedly sterilised. Notwithstanding this, claims for improved effects of in ovo vaccination are making the procedure popular in the poultry industry. The possibility of ensuring pathogen free stock has obvious attractions. Transfer of food and vitamin supplements in ovo, leading to more rapid turnover of stock is financially attractive. From the Journal International Hatchery Practice, 1991, 5 No. 7, 5–9 it is clear that in ovo injection leads to increased hatchability, improved disease resistance, higher growth rates and yield, reduced chick stress and reduced early mortality.

In ovo vaccination improves the protective capability of vaccines by placing them in the embryo at a time when they can stimulate good immunity against disease challenge at an early stage. Accordingly, if the instrument disclosed above could be utilised without perforation of the shell a sustantial advantage should be achieved. However an effective method must introduce the required quantity of materials in time scales that ideally permit thousands of eggs per hour to be treated. Further it is an ongoing problem to print indicia upon cellulosic film and other covering materials utilised in the preparation and storage of food.

The figures which follow i.e. FIGS. 1–15, represent the nearest art of which the inventor is aware. The figures all come from different sources and have never been collocated before.

FIG. 1. Ultrasound diffraction pattern from a 0.75 MHz circular piston transducer produced with Methylene Blue dye solution on white card. Note that precise details of dye pattern depend on the separation of transducer and card surface.

Figure 2:
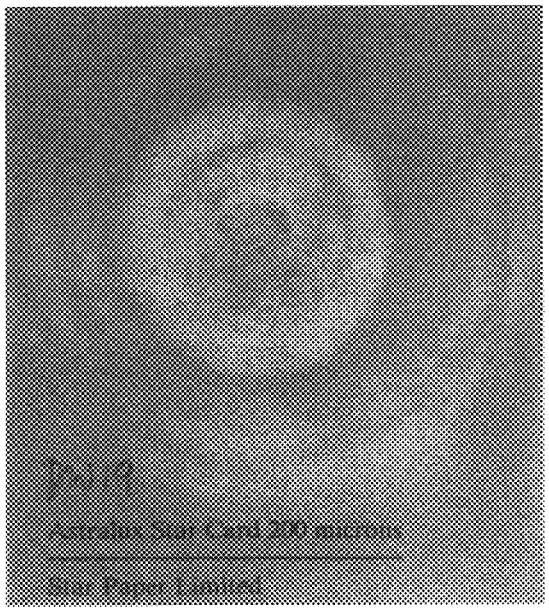

FIG. 2. Diffraction pattern under same conditions as FIG. 1 but in this case Skye Blue [anionic] dye was used.

Figure 3:
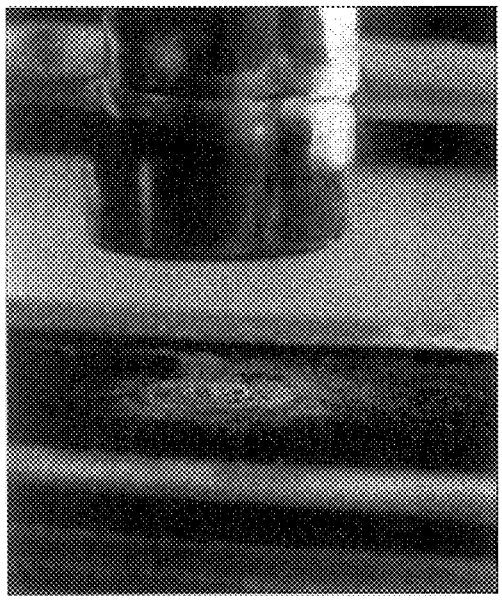

FIG. 3. Bubble cloud on blackened surface produced by ultrasound irradiation and viewed by oblique lighting during sonication at 0.75 MHz.

Figure 4:
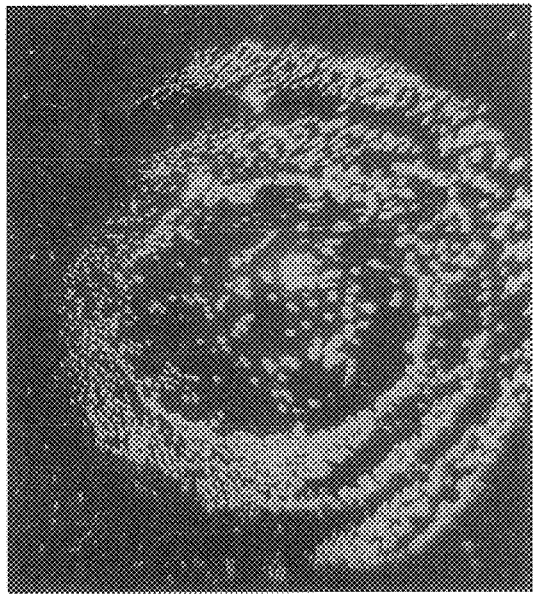

FIG. 4. Bubble mapping produced as in FIG. 3, showing diffraction pattern after ultrasound was switched off. Some smaller bubbles have already disappeared.

Figure 5:
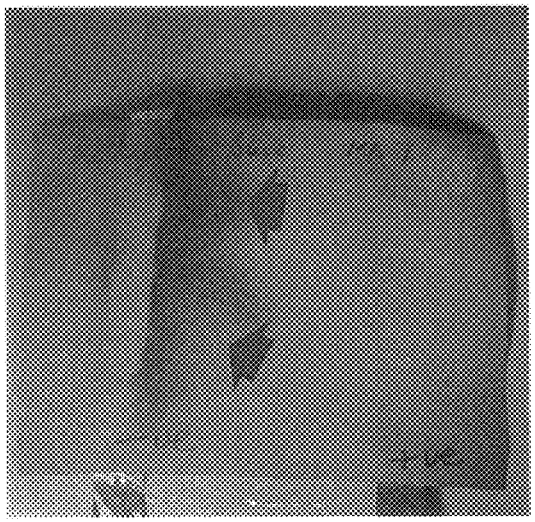

FIG. 5. White card to which electrodes have been attached on the back surface, dipped into Methylene Blue dye solution while a voltage of 1 KV is applied. Dye is deposited close to the negative electrode.

Figure 6:
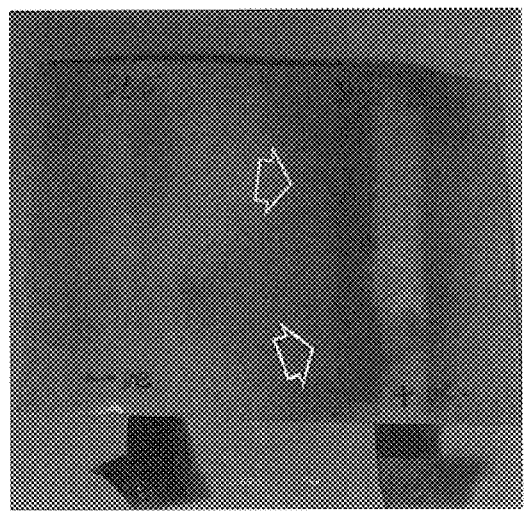

FIG. 6. Same situation as described in FIG. 5 but using Skye Blue dye. The colouration appears on card but in this case around the positive electrode.

Figure 7:
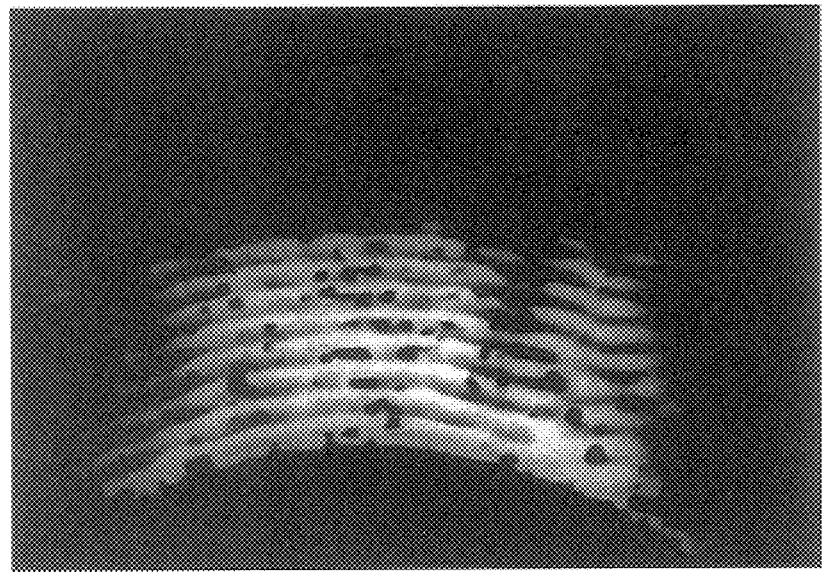

FIG. 7. Schlieren image of egg shell during sonication at 750 KHz. The image shows standing waves and different sized bubbles on the shell surface and others trapped in standing waves.

Figure 8:
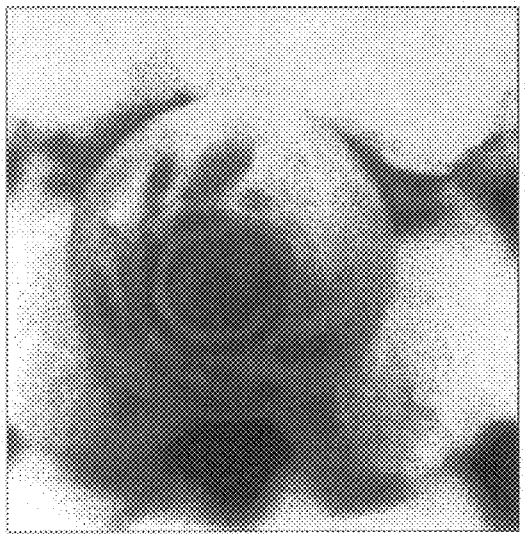

FIG. 8. Diffraction pattern on shell produced by sonication of egg at 750 KHz, the egg was placed in methylene blue dye solution. Note the similarity to the pattern seen in FIG. 1.

Figure 9:
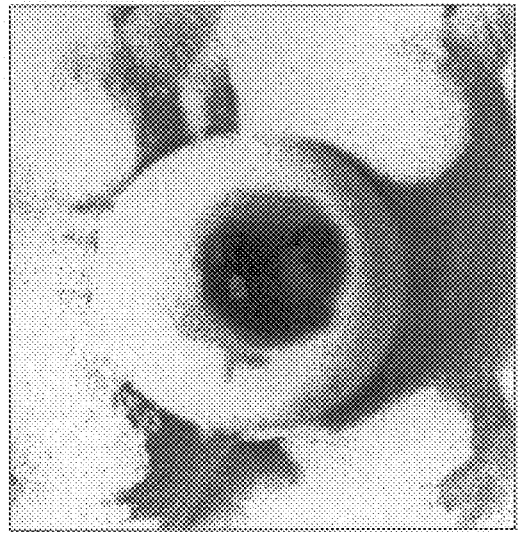

FIG. 9. Dye inside a duck's egg, from which contents were first removed, transported via gas exchange pores under influence of ultrasound at 750 KHz.

Figure 10:
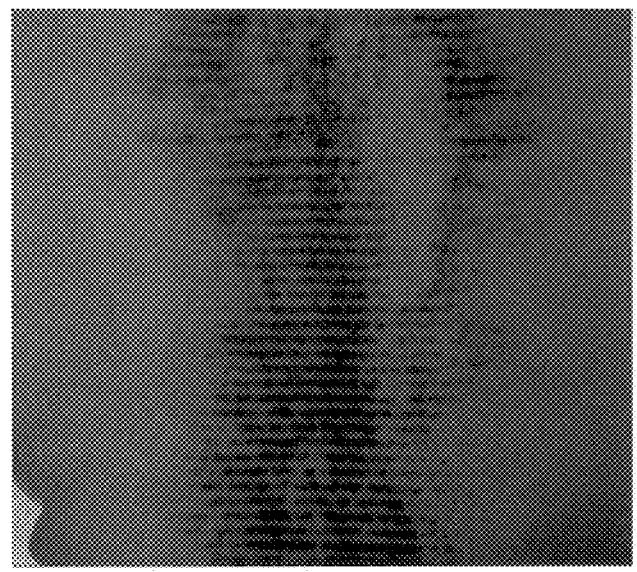

FIG. 10. Standing waves apparent on surface of cut potato deposited by 1 MHz ultrasound in Methylene Blue dye solution. Standing wave was caused by the positioning of an air backed reflector normal to the beam.

Figure 11:
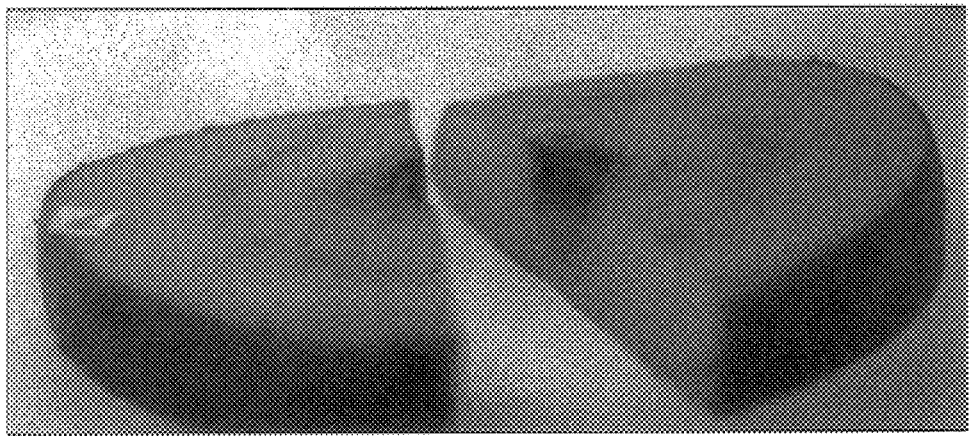

FIG. 11. Penetration of Methylene Blue dye extending about 7 mm into potato under the influence of 750 KHz ultrasound propagating in dye solution.

Figure 12:
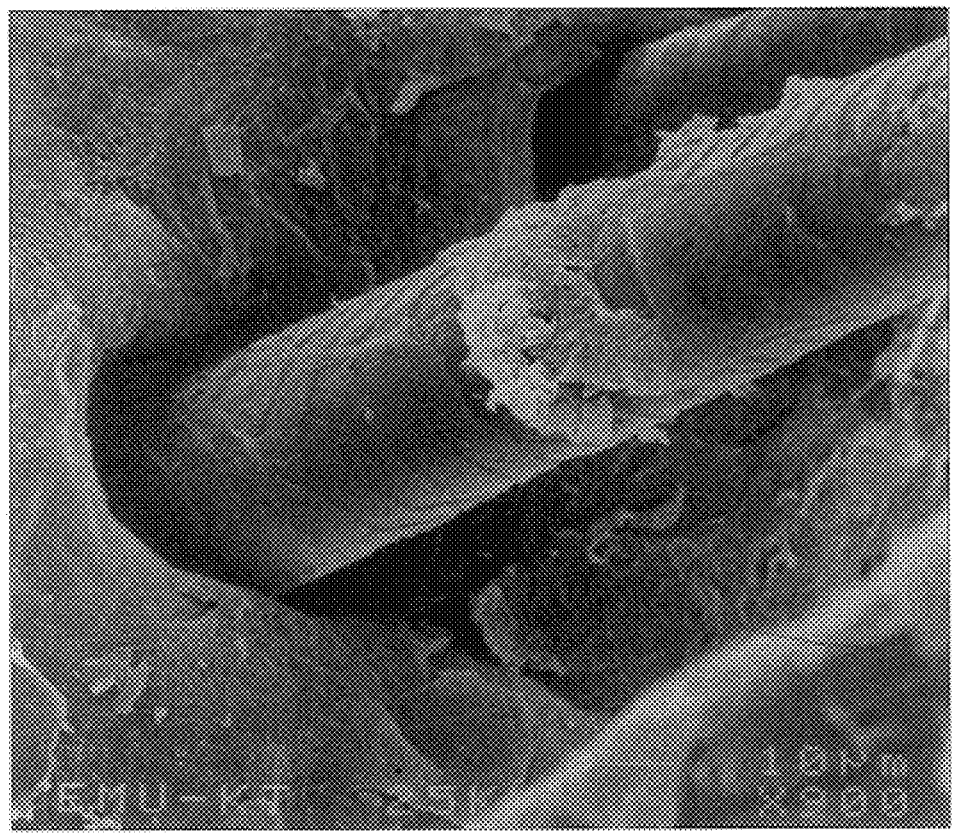

FIG. 12. Scanning electron micrograph of animal skin showing hair shaft and folicles extending below epidermis, providing pathway into the dermis.

Figure 13:
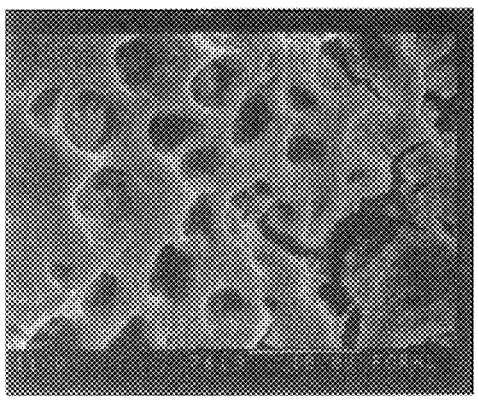

FIG. 13. SEM image of egg shell showing open ends of gas exchange pores and presence of microcracks.

Figure 14:
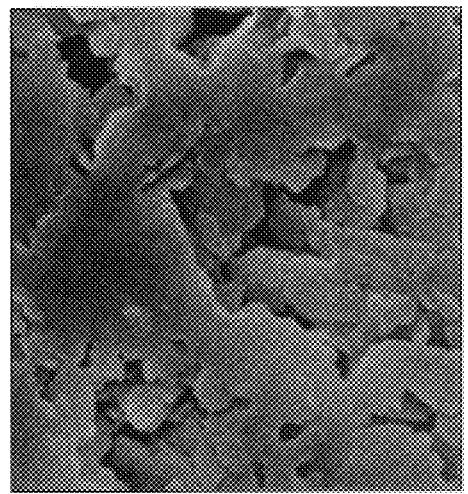

FIG. 14. Irregular spaces seen by SEM in printable card.

Figure 15:
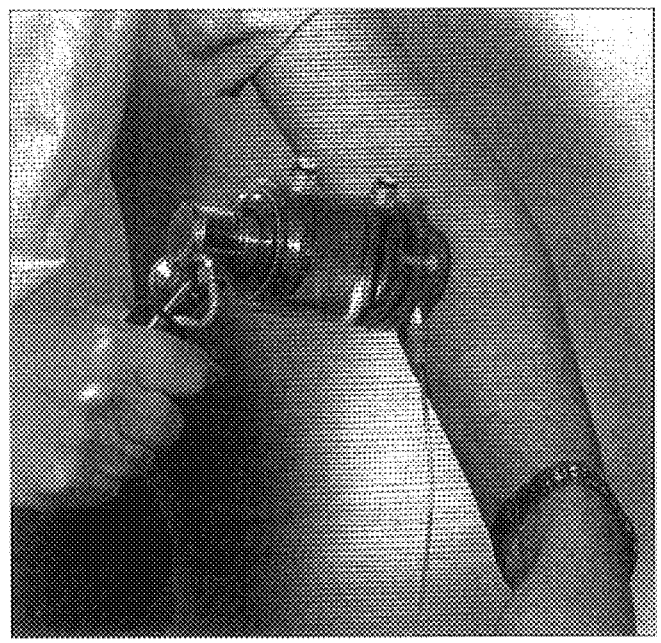

FIG. 15. Example of apparatus to deliver materials transdermally into human subjects using 750 KHz ultrasound.

Figure 16:
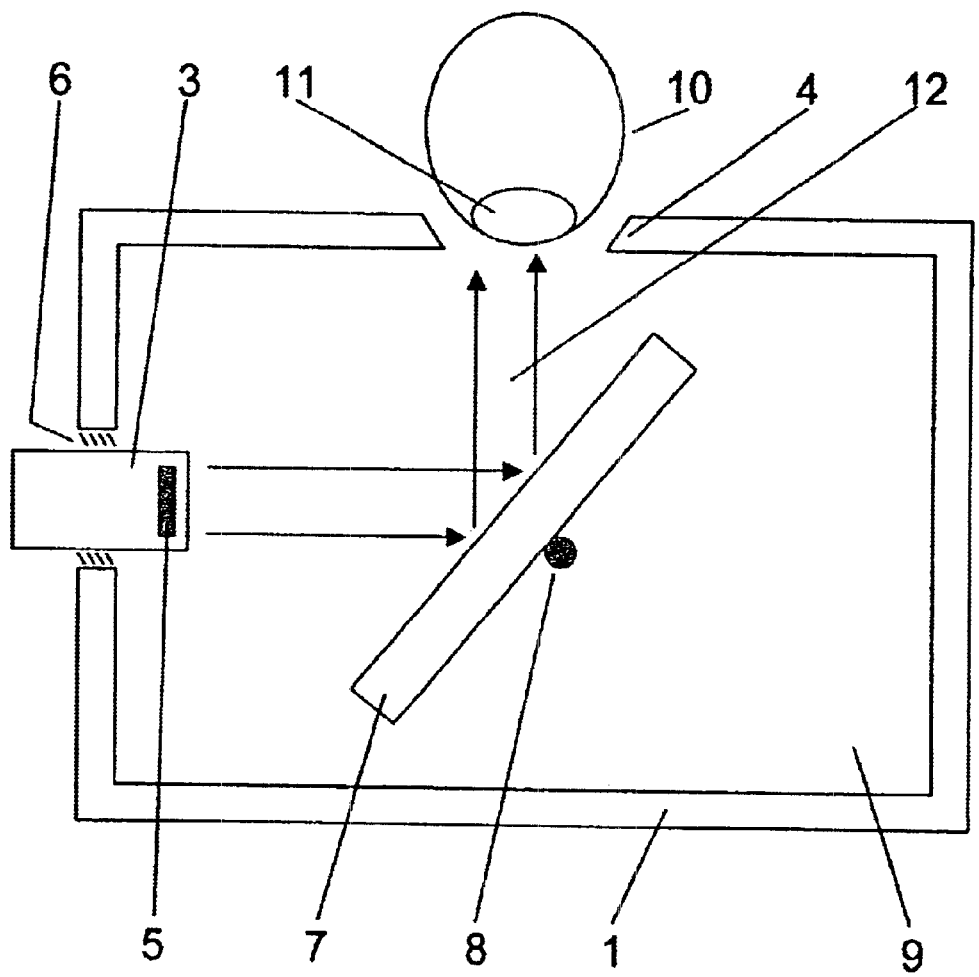

The invention will now be described, by way of illustration only, with reference to the accompanying drawings wherein:

FIG. 16. represents a diagrammatic vertical section through a sonication chamber in accordance with the simpliest form of the present invention.

Figure 17:
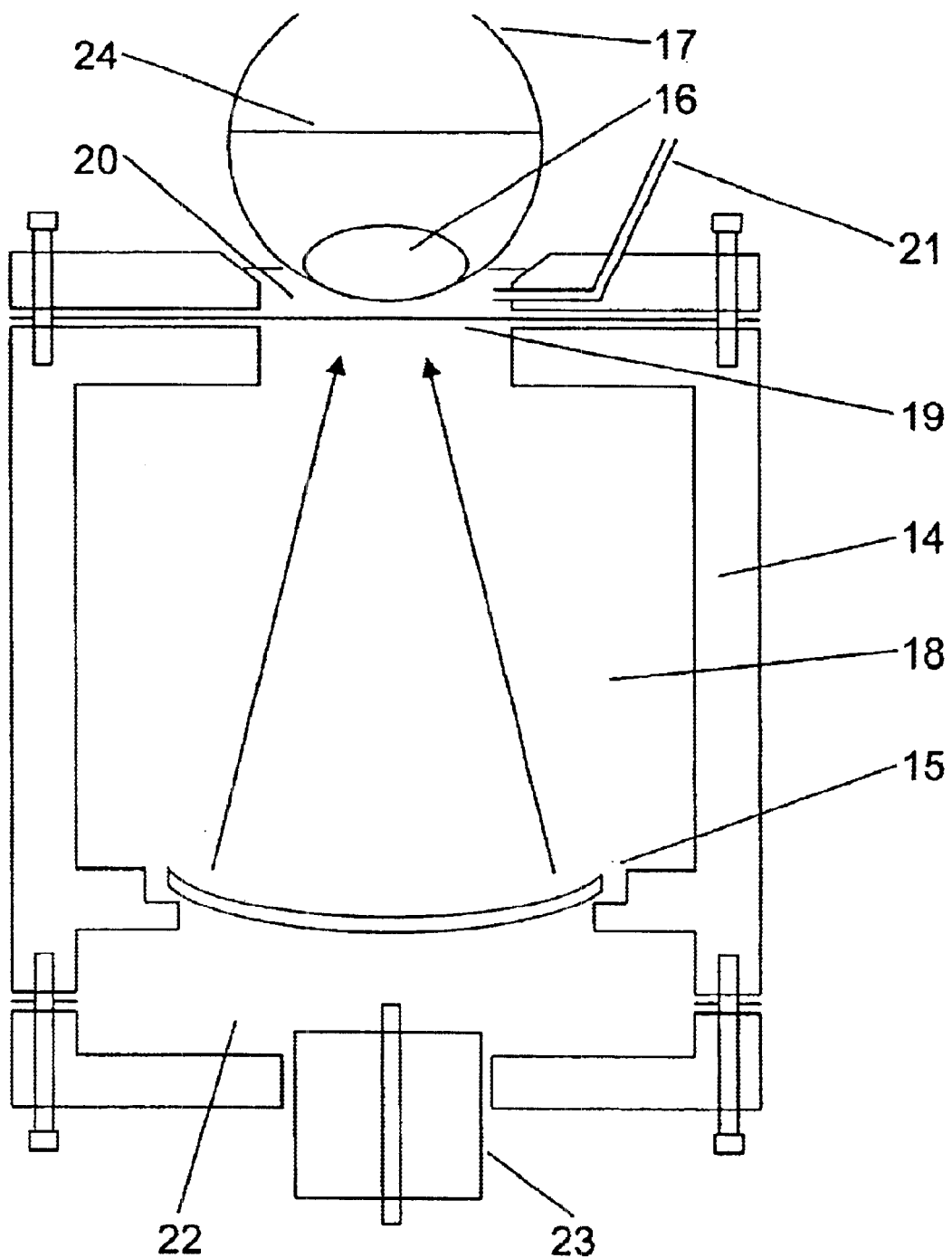
Figure 18:
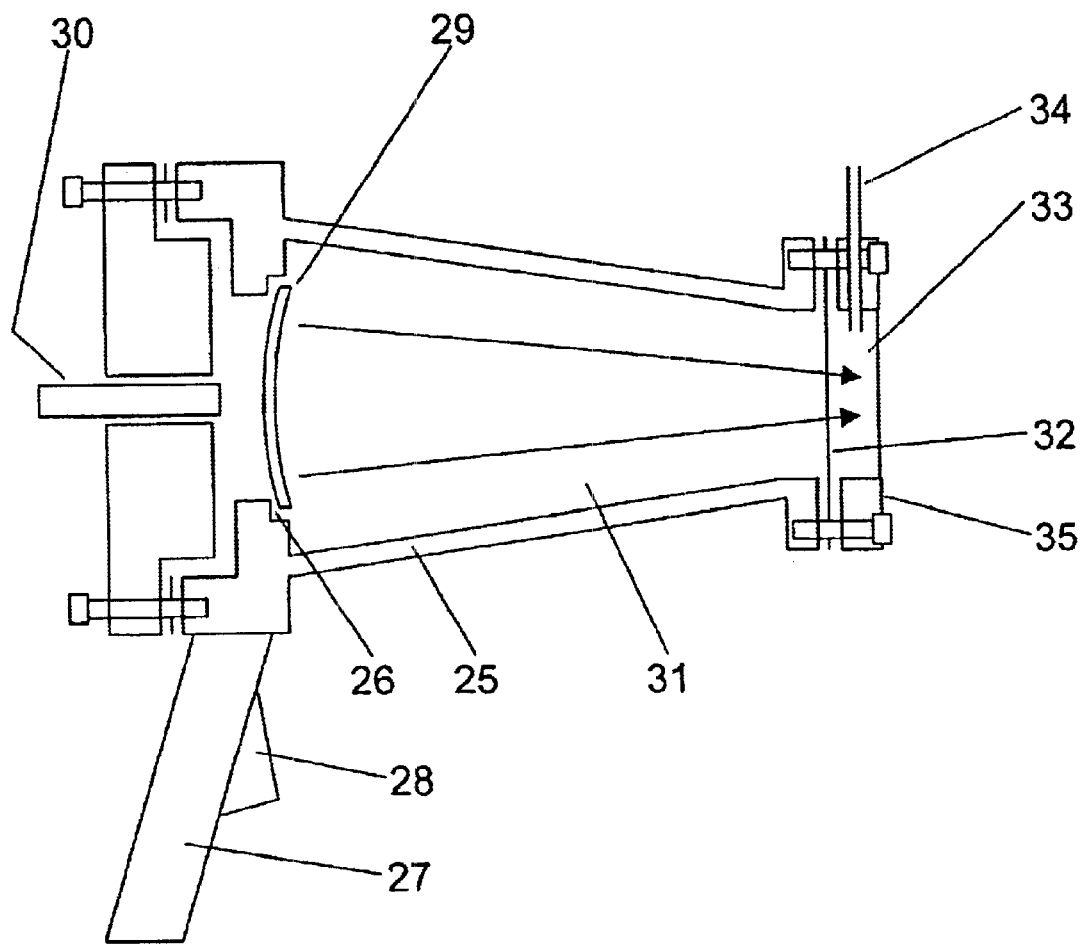

FIG. 17. shows a vertical section through a sonication chamber of a second type for use in the present invention, and FIG. 18. shows a vertical cross-section through an ultrasonic treatment device for use in transdermal applications.

It is known (Shiran M. B., Quan K. M., Watmough D. J., et al (1990). Ultrasonics, 28, November, 411–414.) that the ultrasonic intensity distribution in a given field could be recorded by the concentration of a dye retained on a treated cellulosic paper/card following sonication of this material while submerged in dye solution. FIG. 1 shows an ultrasound-induced diffraction pattern on white card at 750 KHz using Methylene Blue dye and FIG. 2 an inverse pattern obtained using Sky Blue dye. Note that the Methylene Blue is cationic [Venkataraman K. Organic and Biological Chemistry, The Chemistry of synthetic dyes vol 2 Academic Press Inc, New York] and the Skye Blue is anionic. Experiments, (Watmough et al., Med Principles Pract 1994–95, 4, 83–98) have shown that microbubbles generated by the sound field and trapped on the paper surface, map to a close approximation the theoretical intensity [pressure squared] distribution at 0.75 MHz and bubbles of characteristic size are formed on card surfaces over a wide range of frequencies. [See for example, Watmough D. J. [1994]. Ultrasonics 32, No. 4, 315–317]. FIGS. 3 and 4 are examples of acoustically-induced micro-bubble mappings seen only on specially prepared blackened surfaces with careful observation or recorded by photography carried out under oblique lighting conditions.

The relation between the bubble radius R and resonant frequency f is obtained from Minnaert's equation, $R = \frac{1}{2\pi f} \cdot \{3\gamma P/\rho\}^{0.5}$ where P is the pressure in the gas in the bubble, $\gamma$ is the ratio of specific heats and $\rho$ is the density of the fluid. The appearence of white Astralux cards placed in dye solution and then exposed to ultrasound at low kilohertz frequencies was studied. The paper when removed from dye solution and dried revealed the outline of bubbles by virtue of rings or blobs of enhanced dye colouration at sites where bubbles had ocurred. At lower frequencies individual bubbles are seen to be outlined by dye concentrated on their boundaries and recorded by the card. There is evidence that the enhanced dye concentration is associated with changes in electrical potential on surfaces and that the sound causes the changes. FIG. 5 shows a card with +ve and −ve electrodes attached to it and submerged in Methylene Blue dye solution for a short period. The dye colouration appears close to the −ve electrode. FIG. 6 shows the opposite behaviour when Skye Blue, an anionic dye, is used. The clear inference is that electric fields at the surface of recording media and any attached gas/vapour bubbles can be used to redistribute dye colouration.

Accordingly this finding leads to an appreciation of the connection between between enhanced dye concentration on surfaces and ultrasound generated bubble mappings. Initially it was believed that fluid microstreaming around each bubble inhibited formation of a dye depletion layer close to the recording surface. Theoretically this would lead to variations in dye concentration on the paper proportional to sound intensity. [Note that here dye solutions have been used to elucidate the mechanisms of phonophoresis because they enable one to observe the actual processes of transfer across boundaries. For example with an egg shell whose contents have been removed and replaced with distilled water one can observe bursts of dye passing through the shell and can therefore choose ultrasound exposure parameters to optimise the process. The distribution of dye, after short ultrasound exposures, can thus predict the phonophoretic behaviour of other cationic substances in aqueous solution]. We now understand that the situation is more complex since bubbles locally concentrate cationic dyes and dilute anionic dyes. To have a substantial and rapid effect on penetration of dyes or other materials into porous or semi porous surfaces there must be additional mechanism(s) such as bubble collapse. In this cause shock waves and/or microjet formation can be adduced to explain enhanced penetration. Schlieren studies of sonicated surfaces, (See example of sonicated shell surface in FIG. 7) made by the author, demonstrated the occurrence of bubbles, microstreaming around them and shockwave formation caused by their collapse. Due to the size of microjets, at the frequencies studied, this imaging technique does not permit visualisation of the individual jets directly.

FIG. 8 shows the ultrasound-induced diffraction pattern on egg shell caused by ultrasound incident through an aqueous Methylene Blue dye solution on one side of an egg shell (emptied of its contents). With the egg refilled with distilled water it has proved possible to observe spirts of dye (FIG. 9) penetrating the intact part of the shell when the outer surface was sonicated.

In a different context microjets have been observed and recorded by Suslick (see Suslick K. S., The chemical effects of Ultrasound, Scientific American, February 1989). Such jets associated with collapsing bubbles generate fluid velocities of up to 200 m s$^{-1}$. It is easy to imagine the effect we have observed as arising from concentration of dye in solution in the region around micro bubbles and their subsequent collapse producing jets capable of pushing/carrying the dye through some of the gas exchange pores and/or micro-cracks in the shell. The gas trapped in the pores will provide additional nucleation centres for cavitational activity. In other words formation of surface gas bubbles will be aided by the fact that apart from dissolved gas in solution, trapped gas is present in the pores and this will expand under the influence of the sound field. Sonication at medium to high intensity can generate rapid fluid flow in the supporting medium which is called bulk streaming. This flow may also contribute to the phonophoresis process. Phonophoresis may occur with other biological materials.

FIG. 10 shows banding of dye caused by an ultrasound standing wave incident on a cut surface of a potato. The act of cutting damages cells and opens up pathways into the material.

In an effort to discover the most sensitive dye for mapping ultrasound sound fields on surfaces a wide range of dyes were tested and in some instances inverse dye distrubutions were found. Cationic dyes produce enhanced patterns of dye concentration but anionic dyes produce inverse patterns i.e. depleted compared to background concentration. These findings support the idea that ultrasound phonophoresis is at least in part due to changes in surface electrical potential whose cause most probably lies with the interaction of sound (particle vibration) and the surface. Ultrasonically induced microbubbles are clearly a major factor in altering surface charge.

At a gas/liquid interface there is an electrical double layer. In the case of water/air this results in a negative charge at the surface. We have found experimentally that this charge is much larger for gas bubbles, when excited by a sound field, than it is in the absence of a sound field. [See Watmough D. J. et al.(1992) Ultrasonics, 30 (5), 325–331].

Theoretical analysis and calculation reveals that associated with microbubbles is an electric field of intensity $7.5 \times 10^5$ V m$^{-1}$. This finding explains why cationic materials such as dyes are concentrated close to the sonicated surface where the sound intensity is highest. Anionic dyes or negatively charged substances are repelled. Thus cationic materials will accumulate close to the surface and microstreaming and microjet formation, or both, will transfer the material via pores or other channels in the porous surface into the interior of the material or right through it.

Simply directing sound at a surface is not a solution to the problem of phonophoresis. To have commercial benefits, the process of transferring materials across the boundary or into it, must be rapid and thus it has been found that focussing the field with a concave transducer (or lens) can have two beneficial effects. The main field can be restricted to a small area of surface (e.g. portion of the air sac of an egg). Secondly a small chamber, separate from the transducer and its coupling fluid, can be constructed so that only a small quantity of material (e.g. vaccine, nutrients, antibodies or antibiotic), needs to be in direct contact with the treated surface. However having a second chamber requires a thin sonically transparent window separating the first and second chamber. It also imposes a requirement that the liquid in the first chamber, normally water, be thoroughly degassed. Otherwise a bubble screen forms on the membrane surface and blocks/or limits the entry of ultrasound into the second chamber and thus prevents material transfer into the porous surface rather than enhancing it.

FIGS. 12, 13, 14 show the nature of 'porous' surfaces, Astralux card, egg shell and animal skin which are relevant to the present application. Each has microscopic spaces extending from the external surface into the interior of the material or body. According therefore to a first aspect of the present invention, there is provided a method of phonophoretic transfer of an active agent into or across a porous surface, which method comprises contacting the active agent (normally in aqueous solution) and applying thereto ultrasound, preferably in the range of between 20 KHz and 3 MHz, characterised in that the active agent is cationic and is disposed in a low viscosity carrier and thus wherein the said active agent is in direct contact with the porous surface.

The porous surface maybe a human or animal skin, or a shell such as an egg shell, in which case the active agent may be a biologically active agent in an aqueous solution.

The biologically active agent may be selected from one or more vaccines, drugs, nutrients or antibodies. The porous surface may be constituted by a shell of an incubating chicken, duck or turkey egg, in which case the biological agents may include Tylosin tartrate and/or Gentamycin.

In order to reduce the possibility of excessive local heating (caused mainly by the sound field heating the gas content of the bubbles) the ultrasound may be pulsed with appropriate on/off times. Alternatively the air sac end of eggs may be treated so that internal heating becomes unimportant or insignificant. It must be remembered that the surfaces are in good thermal contact with liquid media whose temperature can be kept at or close to ambient.

Alternatively the porous surface may be a printable surface, such as a cellulosic wrapping material, in which case the active agent is a dye disposed in an aqueous carrier associated with a masking means applied to a printable surface prior to phonophoresis of the dye itself.

In a preferred form of the method, ultrasound is focussed through a carrier liquid towards the porous surface and a membrane is disposed between the carrier liquid and the porous surface, whereby the space about the porous surface can be replenished with a supply of active agent to allow for serial transfer to succeeding porous surfaces if desired and without stopping the process.

In a second aspect of the present invention there is provided an apparatus for phonophoretic transfer of an active agent to or through a porous surface, said apparatus comprising, an ultrasonic signal generator, power amplifier, a housing provided with an ultrasound transducer mounted thereon: and a treatment chamber disposed in or on said housing; said transducer being directed towards treatment chamber; wherein the treatment chamber is provided with a liquid tight membrane to retain active agent against porous surface [e.g. skin or shell] located in the treatment chamber during sonication.

In the said apparatus, the housing may be provided with an ultrasound carrier liquid disposed between the transducer and the membrane. The transducer may be focussed either directly towards the porous surface within the treatment chamber, or by means of a deflector within the carrier liquid. The porous surface may be selected from shell, human or animal skin, vegetable material and/or a printable surface. The treatment chamber may be provided with a replenisher conduit whereby the treatment chamber may be recharged with an active agent disposed in an aqueous or other carrier as it is depleted. Preferably the treatment chamber is constructed and arranged to interengage with human or animal skin and to seal thereupon prior to charging the treatment chamber with an active agent for subsequent sonication. The first version of apparatus, with a plane circular unfocussed ultrasound transducer, designed to deliver drugs to human and animal skin is seen in FIG. 15.

In an alternative form of this apparatus, the treatment chamber may include means for introducing a printing mask into the said chamber to allow printing upon the porous printable surface. The mask may be made from an inert substance or alternatively have conducting electrodes so that an external potential may be applied to the mask thus offering the opportunity for enhancement (or reduction) of dye concentration on the recording material.

With reference to FIG. 16 of the accompanying drawings, a perspex chamber (1) which is substantially rectangular in configuration is provided with base, sides and an upper surface; said upper surface defining an aperture to a treatment area (4). The perspex container (1) is provided, in the side, with an aperture through which an air-backed ultrasound transducer (3) is inserted and which may be activated by an external signal generator and amplifier which connect to the PZT element (5) but are not themselves shown in the drawing. The transducer is sealed into the wall with epoxy resin (6). An air-backed acoustical mirror/reflector (7) is placed on a moveable axle (8) and set at roughly 45 degrees, so as to direct ultrasound towards the aperture (4). The perspex apparatus is filled to the brim with an aqueous solution of typically Methylene Blue dye (9), (or other material to be transferred), at a concentration normally of 10 mg l$^{-1}$. An egg (10) is carefully placed in the aperture (4) with the air sac end (11) normally pointing down. To observe the effects of sonication the egg may be cracked open at the pointed end and its contents removed and replaced with distilled degassed water so the air sac can be observed during phonophoresis and if necessary photographs or a video film may be produced. The sound beam (12) is then actuated to cause the biologically active agent in the chamber (9) to transfer across the shell of the egg (10) and into the interior thereof. After a predetermined period of time, the egg (10) may be replaced by a new untreated egg and the process repeated. It will be appreciated that every time an egg is removed, a certain portion of the aqueous active agent is removed with it and accordingly it is necessary periodically to replenish the level of material at (4) by means of the conduit (not shown in FIG. 16). A serial supply of eggs may be provided automatically to the treatment aperture (4) if desired.

With reference to FIG. 17, which shows a vertical section through a perspex apparatus (14) (this is an modified version of that described in FIG. 16) of cylindrical in cross-section. In this case the centrally disposed ultrasound transducer (15) is a focussed bowl and the sound beam from it is directed vertically upwards onto a small portion of shell at the air sac end (16) of an egg (17). The fluid (18) in the main body of the apparatus is distilled degassed water enclosed by an acoustically transparent window (19) which forms the base of the treatment chamber (20). This treatment vessel contains the carrier fluid which can be replaced by means of the conduit (21). The focussed transducer is sealed into the base of chamber (14) and is air-backed (22) with electrical leads from front and back surfaces connected to a BNC connector (23) sealed into the base. Electrical signals from a generator and power amplifier (not shown) excite the transducer and apply acoustic power to the treatment chamber. By removing the egg contents (as seen in the FIG. 9) and replacing same with water (24) very rapid transfer of blue dye (or antibiotic) from the treatment chamber (20) into the interior of the egg can be observed when the power is switched on.

In normal use of the apparatus the incubating eggs are intact before, during and after sonic treatment. The cylindrical apparatus is constructed from three sections, as shown, for ease of sealing the transducer into (lower) floor of apparatus and sealing the membrane into base of the (upper) treatment chamber.

It will be appreciated that the arrangement of FIGS. 16 and 17 can readily be adapted to treat other porous substrates by means of suitable changes.

With reference to FIG. 18 there is provided an apparatus for the ultrasound enhanced or facilitated drug delivery to human or animal skin.

In this arrangement the ultrasound drug delivery device shown generally in the figure is provided with a frusto-conical housing portion (25) and an interconnected cylindrical housing portion (26). The cylindrical portion of the housing is furnished towards the lower side, as shown in FIG. 18, with pistol grip (27), said pistol grip being provided with a trigger (28) for purposes to be described later, The cylindrical housing portion (26) which supports a concave (focussed) ultrasound transducer (29) is provided with a connection conduit to a signal generator and/or amplifier where desired via connector (30). The frusto-conical housing portion is a liquid tight enclosure retaining a carrier medium, for example, degassed water (31) therein. The frusto-conical housing portion (25) is sealed in liquid fashion by means of a membrane (32) remote from the transducer (29), said membrane being acoustically transparent. The liquid filler pipe and the tube for removal of expelled air in the wall of the frusto-conical portion are not shown: both pipes are fitted with screw valves since air or gas must not appear below membrane (32) as it would prevent ultrasound transmission into (33). [See for example, Quan K. M., and Watmough D. J. (1990). Meas. Sci. Technol. 2, 352–357]. This upper chamber carries antibiotic solution or other active agent in carrier fluid and is replenished via conduit (34). The outer surface of (35) is covered by an annular ring of soft rubber sealing material and is placed against animal or human skin and sealed by application of minimal pressure exerted by the operator; filling can be carried out after sealing to skin and appropriate external pressure or suction applied via (34). The trigger can be actuated to control drug delivery either by varying the time of application or intensity of ultrasound or both. The frequency of operation can be varied to choose the size of microbubbles to match the average pore size in the treated surface.

Many experiments were carried out with hens' eggs and duck eggs. All showed diffraction patterns of dye on the outer surface of the shell and penetration of dye into the air-sac end of the egg. The egg shells are perforated by gas exchange pores and minute cracks: it is believed that the dye solution, concentrated around small gas bubbles, is forced down these inlets by radiation pressure or microjet formation or shock waves from collapsing cavities. A combination of these mechanisms may be responsible for transfer across porous boundaries. Another mechanism which cannot be excluded is that ultrasound heats and thus expands the gas in the air sac portion of eggs and causes it to leave by the exchange pores. Then the sound intensity on the shell surface would drop due to changed sound reflection coefficient. The temperature and pressure [below ambient] in the air sac would drop thus sucking in dye solution. This process could act very rapidly and repeatedly as bubbles on the shell surface first appear then are swept away. It was found that at the intensities initially employed [1–3 W $cm^{-2}$ spatial average] the rate of transfer of dye and antibiotic is relatively low and the quantity of material required to fill the chamber is large. Increasing the sound intensity and/or exposure time enhances dye/antibiotic transfer.

To overcome any limitations of the apparatus shown in FIG. 16, an improved focussed apparatus was developed and is shown in FIG. 17. This increases the quantity of drug or dye transferable by phonphoresis by incorporating a focussed transducer directed at the shell. By including two separate chambers connected by an acoustically transparent window, the quantity of drug or other substance to charge the device can be much reduced with this arrangement. The chamber next to the transducer is filled with distilled, degassed liquid, normally water. The investigation reported herein explains why many investigators have failed to achieve useful transfer of materials through porous surfaces. Clearly, for ultrasound to create bubbles on a surface at modest intensities, it requires for preference an aqueous solution of a biologically active material such as a drug. These have the lowest intensity threshold for onset of cavitation. Preferably the viscosity should be low to facilitate vigorous microstreaming and microjet formation. Previously, of course ointments have generally been utilised for phonophoresis, but this is an indication that the mechanism whereby transfer is effected has not been generally understood and may explain the conclusion of Williams, (Ultrasonics 1990, 28, 132–136) relating to the efficacy of phonophoretic transfer. The surface into which drugs are to be transferred should be porous. The carrier solution should be in direct contact with the skin or shell, or other porous surface, which of course presents practical if not insurmountable obstacles, and this may be why ointments have been tried previously as they offer an easy way to keep the drug in contact with the surface [without a containing vessel] and provide a way of coupling the ultrasound transducer.

In order to confirm that our understanding of phonophoresis has wider validity than the application to eggs, we have applied the principle to successfully achieve enhanced transfer of methylene blue dye into potatoes, card, cotton cloth, skin and chickens legs.

The experiments all demonstrated diffraction patterns on the surfaces at a much higher concentration than background levels and enhanced transfer through surfaces. Further it was found that when pig skin was cleaned with methanol prior to phonophoresis a much higher level of transfer occurred. This finding indicates that had we used ointment, as earlier workers have chosen to do, the pores would have been blocked and the substance would not have permitted formation of gas filled cavities at or near the surface. [Transfer of drugs would have been inhibited rather than enhanced.] This would also prevent formation of any electrical field and stop the mechanism(s) necessary for transfer across the boundaries. This is in part because ointments generally prevent aqueous solutions from wetting the surface; this fact alone would be enough to reduce bubbles forming on skin.

Experiments using a Schlieren optical system with sonicated eggs observed within a tank of water have shown conclusively that ultrasound does cause standing waves around the shell and causes appearence of gas/vapour filled bubbles on the shell surface. Clear evidence of microstreaming around bubbles and shock wave formation was found. Slices of potato were also studied during sonication in the same Schlieren optical system. Standing waves, bubble formation, microstreaming, surface effects and enhanced ingress of dye at sites of highest sound intensity were found on a large number of samples.

Observation of phonophoretic dye transfer by ultrasound treatment indicated that with continuous wave ultrasound it is preferable to direct ultrasound to the air-sac end of eggs. Once a material penetrates the shell, a relative slow process of redistribution by diffusion in the interior of the egg will be acceptable. The use of the air sac end of the egg avoids biological damage to the incubating egg and permits higher intensity levels to be safely employed. When the technique is applied to the skin, interrupting the sound by pulsing it permits bubble formation while avoiding excessive heating.

The apparatus shown in FIGS. 16, 17 and 18 does not show the ultrasonic generator the output from which in each case is connected to the front and back surfaces of the transducer. This may be chosen to operate at any convenient frequency between 20 KHz and 3 MHz. Most of our egg studies were carried out at around 1 MHz however the lowest possible frequency is normally preferred because cavitation occurs more readily at lower frequencies and unwanted heating effects are minimised. Sound also penetrates deeper into human and animal tissues at lower frequencies. The size of pores in shells may place an opposite constraint on the chosen frequency so that our results with dyes and egg shells may already be optimised close to 1 MHz. In the embodiments as shown in FIGS. 16 and 17, a series of chambers may be arranged so that eggs can be supplied sequentially to each of a series of devices for phonophoresis. An automatic egg handling system can feed eggs into the treatment chambers and can remove the same after sonication.

In order to transfer drugs into patients or animals, the cylindrical apparatus shown in FIG. 17, can be narrowed down to a cone and the lower chamber filled with degassed distilled water to permit efficient transfer of acoustic waves into the upper compartment. At the same time the device can be made smaller such that it may be placed on the skin with the drug compartment empty. The rim of the compartment is provided with a seal [rubber or similar material] and a drug or vaccine, or other biologically active material, can be delivered down a filler pipe and the material sonicated until sufficient transfer has taken place.

A lower powered device, which may be left in contact with the skin of a patient or animal for protracted treatments, is envisaged. Such a role may be required for slow transfer of topical drugs, such as anticancer agents where oral delivery or injection by hypodermic needle would cause unwanted side effects such as hair loss or nausea (See for example, Tyle and Agrawala; Drug delivery by phonophoresis: Pharmaceutical Res., 6, No., 5, 1989). Where drugs have to be injected daily, such as for diabetes, the apparatus can obviate the associated trauma. It will be appreciated that the skin is connected to underlying tissues by various 'channels' such as sebaceous glands, follicles, and sweat ducts, and transfer can also take place through channels between cells and by diffusion through cells. In the application of this invention to the medical art it will be appreciated that patients need to have the advantage of non-invasive transfer because of AIDS and the concurrent problem of needle-stick Where slow transfer of a biologically active agent is desirable, a portable battery-operated apparatus in accordance with FIGS. 16, 17 and 18, but duly adapted, is desirable.

The invention relates, therefore, to a method of phonophoresis and to forms of apparatus for achieving it. The invention further provides a method of transdermal administration of biologically active agents to a subject by means of phonophoresis.

What is claimed is:

1. An apparatus for phonophoretic transfer of an active agent to or through a porous surface, said apparatus comprising an ultrasonic generator, a housing provided with an ultrasound transducer mounted in or on the housing, and a treatment chamber disposed in or on said housing, said transducer being directed towards said treatment chamber, wherein the treatment chamber is separated into a first chamber portion and a second chamber portion by an acoustically transparent liquid-tight membrane, the transducer being disposed in the first chamber portion and the first chamber portion being arranged in use to retain a carrier medium, and the second chamber portion being arranged to retain therein the active agent against a porous surface located against the second chamber portion during sonication.

2. An apparatus according to claim 1 wherein the housing is provided with an ultrasound carrier liquid disposed between the transducer and membrane.

3. An apparatus according to claim 2 wherein the transducer is selected from the group consisting of a transducer focused directly upon the porous surface within the treatment chamber, and a transducer focused by means of a deflector within the carrier liquid which deflector is adapted to focus the sound upon the porous surface.

4. An apparatus according to any one of claim 1, 2, or 3 wherein the porous surface is selected from the group consisting of an egg shell, human skin, animal skin and a printable surface.

5. An apparatus according to any one of claim 1, 2, or 3 wherein the first chamber portion is provided with a replenisher conduit.

6. An apparatus according to any one of claim 1, 2, or 3, wherein the treatment chamber is constructed and arranged to interengage with the porous surface and to seal thereupon prior to charging of the treatment chamber with a biologically active agent for subsequent sonication.

* * * * *